United States Patent

Freeman et al.

[11] Patent Number: 6,016,193
[45] Date of Patent: Jan. 18, 2000

[54] CUVETTE HOLDER FOR COAGULATION ASSAY TEST

[75] Inventors: Gary Freeman; Christopher Mauer, both of Palm City, Fla.

[73] Assignee: Awareness Technology, Inc., Palm City, Fla.

[21] Appl. No.: 09/103,094

[22] Filed: Jun. 23, 1998

[51] Int. Cl.[7] .................................................. G01N 21/47
[52] U.S. Cl. ............................................. 356/244; 356/39
[58] Field of Search ........................... 356/39, 244, 440; 433/133; 73/54.15; 422/73

[56] References Cited

U.S. PATENT DOCUMENTS

| | | | |
|---|---|---|---|
| 3,790,346 | 2/1974 | Ritchie | 73/54.15 |
| 3,947,122 | 3/1976 | Walker . | |
| 3,967,934 | 7/1976 | Seitz et al. | 73/54.15 |
| 5,331,398 | 7/1994 | Eggl . | |
| 5,372,946 | 12/1994 | Cusak . | |
| 5,504,011 | 4/1996 | Gavin . | |
| 5,522,255 | 6/1996 | Neel . | |
| 5,534,226 | 7/1996 | Gavin . | |
| 5,743,718 | 4/1998 | Mendoza et al. | 422/73 |

Primary Examiner—Robert H. Kim
Assistant Examiner—Tu T. Nguyen
Attorney, Agent, or Firm—Oldham & Oldham Co., LPA

[57] ABSTRACT

A cuvette holder is provided to allow a flow cell optical analyzer to be adapted for coagulation analysis. The flow cell analyzer has a light source and a photo detector defining a first and a second end of an optical path, a vacuum source for drawing a liquid sample through a flow cell positioned in the optical path so that light from the light source passes through the sample, and means for analyzing data collected at the photo detector. The coagulation analyzer has a light source and a photo detector defining the respective ends of an optical path, a cuvette containing a liquid sample positioned in the optical path for passage of light from the light source through the liquid sample, a means for agitating the liquid sample and a means for analyzing data collected at the photo detector. The adaptation is achieved by removing the flow cell and replacing the flow cell with a cuvette holder comprising an opening for receiving and holding the cuvette in the light path and communicating the vacuum source to the cuvette holder, the means for agitating provided by a magnetic stirring bar in the cuvette, the stirring bar being magnetically coupled to a rotor rotatably mounted in a rotor housing below the cuvette and having a permanent magnet mounted on a top surface thereof, wherein the rotor is rotated in the rotor housing by an air pressure differential in the rotor housing created by the communication of the vacuum source to the cuvette holder.

9 Claims, 2 Drawing Sheets

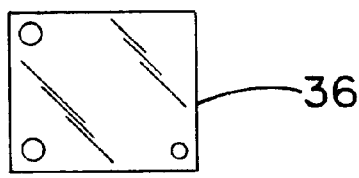
FIG.-6
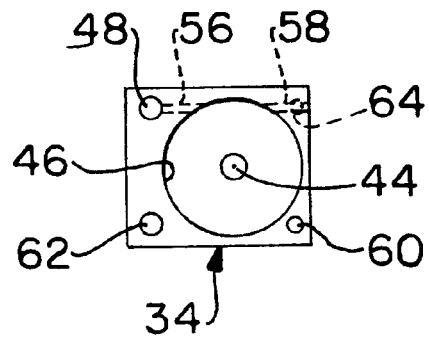
FIG.-7
FIG.-8
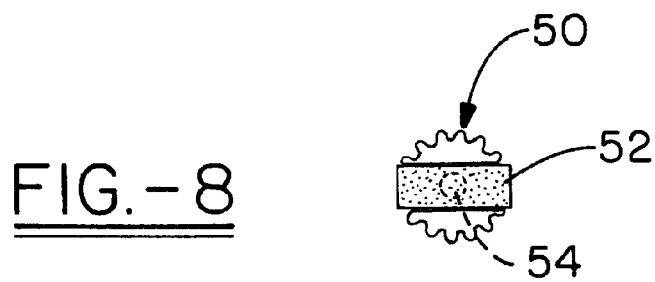
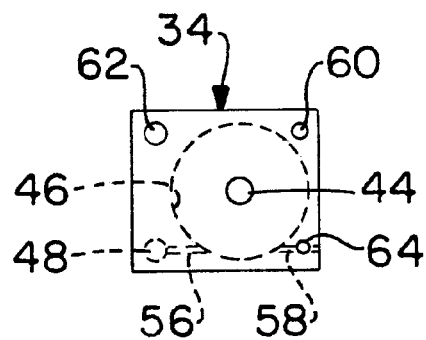
FIG.-9

CUVETTE HOLDER FOR COAGULATION ASSAY TEST

The present invention relates to a holder for containing a cuvette, particularly a cuvette used in a chemical analysis requiring agitation of the test material in the cuvette. More particularly, the invention relates to a cuvette holder having an impeller with a magnetic rod mounted thereupon built into the cuvette holder, so that when the impeller is caused to turn by an air pressure differential across the impeller, the moving magnetic rod causes rotation of a magnetic stirring bar contained within the cuvette. Even more particularly, the present invention allows an optical analysis apparatus having a vacuum source to be provided with a magnetic stirring source for the sample.

BACKGROUND OF THE ART

In conducting certain testing on bodily fluids such as blood, it is necessary to analyze the time that it takes the specimen to coagulate under certain specified conditions. In such a testing apparatus, it is common practice to use disposable sample containers, typically called cuvettes. When the specimen is placed in the cuvette, it is necessary to also place a small magnetic stirring rod in the cuvette to provide agitation to the specimen necessary to cause the coagulation. Because of the small size of the cuvettes and because of a need to not contaminate the side surfaces of the cuvette with fingerprints and the like when a photo-optical technique is being used for analyzing the coagulation progress, it is desirable to provide a cuvette holder which retains the cuvette in fixed spatial relationship to an optical path through the holder provided by apertures in the holder sides. It is also desirable to provide a cuvette holder having an impeller with a magnetic bar mounted on the impeller, so that the magnetic field induced by rotation of the impeller can cause a magnetic stirring rod contained within the cuvette to rotate in a complementary fashion.

A clinical calorimeter is an instrument which employs color filters, a light source, a sample holder, typically either a holder for interchangeable cuvettes or a flow cell, and a photo detector. In an aspirating system, a controlled vacuum source is used to draw the sample under test into a flow cell aligned with the light path defined by the light source and the photo detector. Measurements of the absorbance or transmission of the light by the sample are made and used to determine quantitatively such analytes as glucose, cholesterol, enzymes, etc. The temperature of the samples is carefully controlled. Because the clinical calorimeter aspirates the sample from the cuvette, the clinical calorimeter is not provided with means to agitate the sample.

A coagulation meter as is generally known in the prior art has a light source, a photo detector, a timer and a stirring means to determine the level of clotting agents in a serum sample. The reaction cuvette used is a vial containing a stir bar, which is magnetically coupled with a rotating magnetic source located in the coagulation meter. By knowing the time necessary for a clot to form on the stir bar and the temperature at which the test is conducted, the level of clotting agents present in a serum sample may be determined.

It is a desirable yet unachieved goal of the prior art to provide a cuvette holder which allows a clinical calorimeter to perform the function of the coagulation meter without sacrificing the advantages of the existing features.

SUMMARY OF THE INVENTION

It is therefore an object of the present invention to provide a device for holding a cuvette in a light path provided by an analytical instrument. The cuvette would contain a magnetic stirring bar to agitate the contents of the cuvette while in the light path. The device comprises an upper portion and a lower portion. The upper portion has an opening for receiving and holding the cuvette. The lower portion is affixed to the upper portion and comprises a rotor housing and a rotor, the rotor rotatably mounted in the rotor housing and having a permanent magnet mounted on a top surface thereof, such that the rotation of the rotor in the rotor housing induces a magnetic field which causes co-rotation of the stirring bar.

BRIEF DESCRIPTION OF THE DRAWINGS

Better understanding of the present invention will be had when reference is made to the accompanying drawings, wherein identical reference numerals are used to identify identical parts and wherein:

FIG. 6 shows a top plan view of the separator plate of the present invention;

FIG. 7 shows a top plan view of a bottom section of the present invention;

FIG. 8 shows a top plan view of the rotor assembly of the present invention; and FIG. 9 shows a bottom plan view of the bottom section of the present invention.

DETAILED DESCRIPTION OF THE INVENTION

Figure 1:
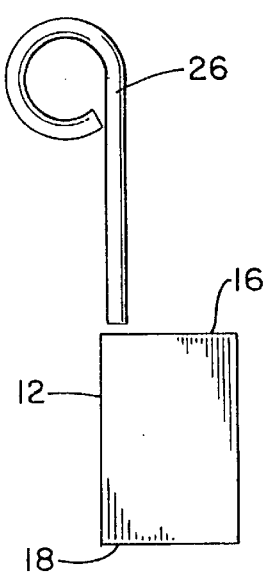
FIG. 1 shows a right side elevation view of the upper section of the device of the present invention in a partially assembled state.
Figure 2:
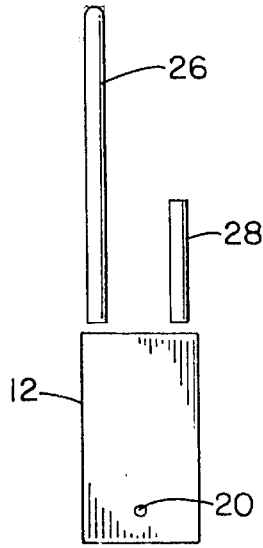
FIG. 2 shows a front elevation view of the upper section of the device of the present invention in the same partially assembled condition of FIG. 1.
Figure 4:
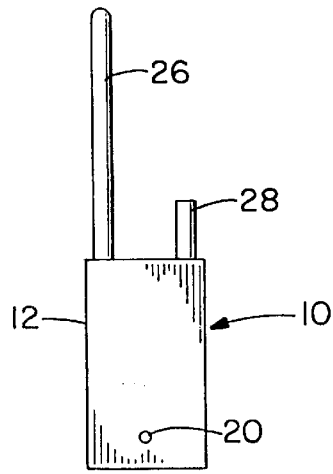
FIG. 4 shows the front elevation view of the upper section of the device of the present invention in an assembled condition.
Figure 3:
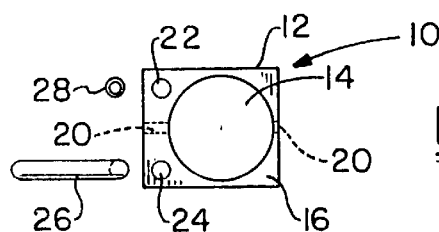
FIG. 3 shows a top plan view of the device.
Figure 5:
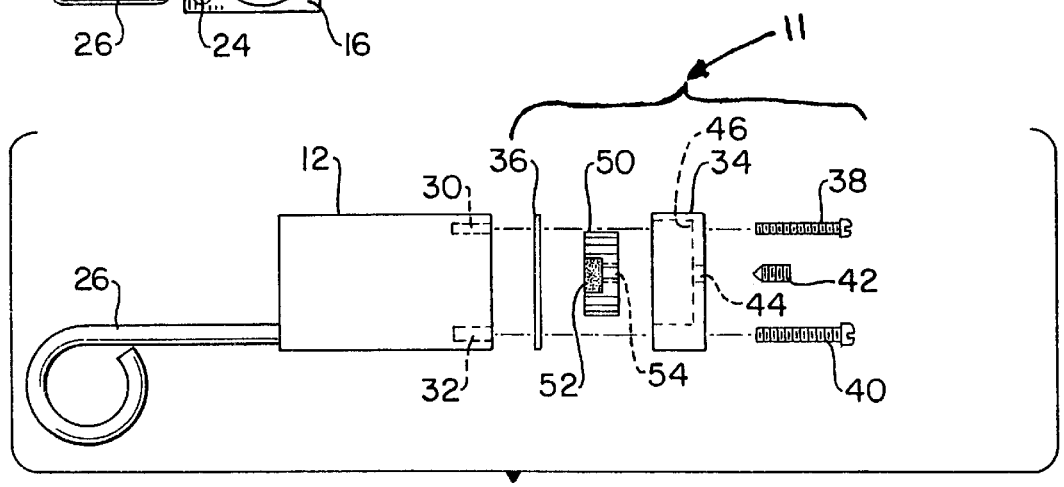
FIG. 5 shows an exploded view of the full device of the present invention.

FIGS. 1 through 4 show the top portion 10 of the present invention cuvette holder in front, side, top and assembled side views, and FIG. 5 shows the entire cuvette holder, including the bottom portion 11. The top portion 10 of the present invention comprises a generally rectangular solid body 12 having a cylindrical bore 14 formed therethrough. The body 12 is preferably formed from a metallic material, particularly a metal which may have an anodized finish placed thereupon. As best seen in FIG. 3, the cylindrical bore 14 is generally centered and passes from a top surface 16 of the rectangular solid body 12 to a bottom surface 18. Intersecting the cylindrical bore 14 and directed normally thereto, preferentially at a diameter of the cylindrical bore, is a smaller aperture 20 which serves as an optical viewing port for a light beam provided by the test apparatus used. This smaller aperture 20 is seen in FIGS. 2–4, but not shown in FIG. 1, as it passes from the front to the back surface of the rectangular solid body 12. In addition to the cylindrical bore 14 through the rectangular solid body 12, the top surface 16 is provided with two additional bores 22 and 24, which are generally located in adjacent corners of the top surface 16. Bore 14 may be moved off center slightly, as is shown in FIG. 3, to accommodate holes 22 and 24. The first of these, bore 22, passes entirely through the rectangular solid body 12 parallel to the cylindrical bore 14. The second bore 24 extends only a partial distance through the rectangular solid body 12 from the top surface 16. This second bore 24 is sized and adapted for receiving and securing a handle member 26 used to place the device into the test apparatus and to remove it therefrom. Although a particular shape of the handle member is shown in FIGS. 1–4, this particular shape of handle is shown for illustrative purposes only and other variations are certainly available. The first bore 22 is sized and adapted to frictionally receive and retain a short length of tubing 28, preferably metallic tubing. The tubing should be sized with an outside diameter suitable for frictional engagement with a tube supplying vacuum to the analyzer with which this device will be used.

In addition to the cylindrical bore 14 and the first bore 22, the bottom surface 18 of the rectangular solid body 12 is provided with two threaded bores 30, 32 for receiving screws, as will be described below. These bores 30, 32 will typically be placed in the corners of the rectangular solid body 12 other than the corner in which the first bore 22 is made. Cylindrical bore 14 is sized so that it will receive a cuvette, usually a disposable cuvette, of the type in which the fluid being analyzed is contained. When placed in the bore 14, a closed end of the cuvette will be towards bottom surface 18 and an open end of the cuvette will be towards top surface 16, with fluid contained within the cuvette effectively in an optical path provided by bore 20 and such that a magnetic stirring bar placed in the cuvette is below, that is, towards surface 18, the optical path.

Further assembly of the cuvette holder device is revealed by reference to FIG. 5, which shows the entire device in an exploded right side view, including the bottom portion 11. In completing assembly of the cuvette holder, a rotor housing 34 and a housing cover 36 are attached to the bottom surface 18 of the rectangular solid body 12. Both the housing cover 36 and the rotor housing 34 are provided with corner-positioned apertures which may be aligned with the two screw-receiving bores 30, 32 in the bottom surface 18. Of these, apertures 60 and 62 in housing 34 receive screws 38 and 40 when the screws are passed through them and into bores 30, 32, respectively. Similarly, apertures 61, 63 in the housing cover 36 correspond to apertures 60, 62. In this manner, housing cover 36 and rotor housing 34 may be removably secured to the bottom surface 18. When this is done, the cover 36 and housing 34 define a chamber for containing a rotor, as will be described below.

Further details of the housing cover 36 are seen in FIG. 6, which shows the housing cover in top plan view instead of the side view in which it is shown in FIG. 5. As indicated in the drawing, the preference is to provide a transparent housing cover, usually from a polymeric material, so that the interior of the rotor chamber may be observed through the bore 14 in the rectangular solid body 12. Likewise, FIGS. 7 and 9 show further details of the rotor housing 34.

In addition to the apertures 61, 63 for receiving screws 38, 40, housing cover 36 has a third corner-positioned aperture 43, which is aligned with bore 22 so that bore 22 is in communication with the rotor housing 34 when the rotor housing and housing cover attached to rectangular solid body 12. When this communication is established, bore 48 in the rotor housing effectively becomes an extension of bore 22. Acting with bore 56, it communicates the chamber in the rotor housing with tube 28.

The rotor housing 34 is generally hollow due to a large bore 46 and has a centrally positioned internally-threaded aperture 44, which is concentric with large bore 46. It also has a small conduit comprising co-linear bores 56, 58 made through a side wall of the housing 34 and communicating bore 48 with the exterior of the rotor housing 34. A further bore 64, positioned normal to bore 58 and originating from the bottom surface of the rotor housing also intersects bore 58. Rotor housing 34, like the housing cover 36, has a footprint essentially identical to that of the rectangular solid 12. A cone set screw 42 placed in the central aperture 44 provides a pivot point upon which a rotor 50 with peripheral impeller members may be seated for rotation thereupon.

As is seen in FIG. 8, the rotor 50 is typically comprised of a lightweight non-metallic material, preferably a polymeric material. The rotor 50 has a slot 51 on a top surface thereof and an axial aperture 54 therethrough. When a rectangular bar 52 of a magnetic material sized for being received in slot 51 is placed in the slot and retained therein, the rectangular bar effectively closes off the aperture 54, providing a seat for cone set screw 42. The retention of magnetic bar 52 in slot 51 may be through frictional fit, adhesive, or a variety of known means. The periphery of the rotor 50 is provided with a plurality of vanes 57 or the like to act as impellers. If an air pressure difference is induced across the inside of the rotor housing 34, air will flow from either the side wall bores 58, 64 to the first bore 22 or in the opposite direction, but in either case the air flow will cause movement of the vanes 57 and rotation of the rotor 50. When the rotor 50 is positioned immediately below and coaxial to the central aperture 14 in the rectangular solid 12, and a cuvette containing a magnetic stirring bar is positioned in the bottom of the central aperture, the magnetic field induced by the rotation of the magnet 52 mounted on the top of the rotor 50 will cause rotation of the stirring bar in the cuvette. This will effect agitation of the sample in the cuvette. In order to achieve this objective, rotor 50 must be sized in diameter and thickness such that it does not impinge on the surfaces of the rotor housing in any way which would impede free rotation.

When the cuvette holder of the present invention is used in a non-conventional apparatus for conducting the coagulation assay test, such as a calorimetric apparatus, the apparatus will typically be provided with an aspirator line and a vacuum pump. By attaching the aspirator feature to the tubing 28 protruding from aperture 22, the vacuum pump feature of the apparatus can be used to draw a vacuum on the rotor housing 34, thereby inducing a flow of air into the rotor housing 34 through the side wall aperture 56 and 58. This flow of air, caused by the pressure differential caused by the vacuum pump, will cause the rotor 50 to turn. The use of the cuvette holder of the present invention permits a colorimeter apparatus to be adapted to conduct photo-optical detection of coagulation and also allows easy and reliable insertion and removal of test cuvettes from the test cell and instrument.

Although the specific application taught by this disclosure describes the use of this device for rotating a magnetic stirring bar in a cuvette used in a coagulation test, it will be recognized that a variety of chemical tests involve analysis of light passing through a cuvette containing a fluid which requires agitation as would be provided by a magnetic stirring bar. The present invention should find application in these devices.

What is claimed is:

1. A device for holding a cuvette in a light path provided by an analytical instrument having a source of air pressure differential, said cuvette containing a magnetic stirring bar to agitate the contents of the cuvette while in the light path, said device comprising:

an upper portion having an opening for receiving and holding the cuvette; and a lower portion affixed to the upper portion and comprising a rotor housing and a rotor, the rotor having a permanent magnet mounted on a top surface thereof and a plurality of vanes, the rotor being rotatably mounted in the rotor housing;

the rotor housing having a first bore in which the rotor is seated and second and third bores communicating the first bore with the exterior of the device, so that air flow may be induced from an external air pressure differential source across the first bore from the second bore to the third bore, the second and third bores being situated so as to direct the air flow at the plurality of vanes to cause rotation of the rotor within the first bore;

wherein the rotation of the rotor in the rotor housing induces a magnetic field which causes co-rotation of the stirring bar.

2. The device of claim 1 wherein the second bore is communicated with the exterior of the device through a longitudinal bore in the upper portion, the longitudinal bore being communicated with the second bore.

3. The device of claim 2 wherein the longitudinal bore is adapted at one end thereof for attachment to the air pressure differential source.

4. The device of claim 1 wherein the opening in the upper portion for receiving the cuvette is a longitudinal cylindrical bore.

5. The device of claim 4 wherein the longitudinal cylindrical bore and the rotor are coaxial when the lower portion is affixed to the upper portion.

6. The device of claim 4 wherein the upper portion further has an optical path formed therethrough by a transverse bore in the upper portion.

7. The device of claim 6 wherein the transverse bore passes diametrically through the longitudinal cylindrical bore.

8. The device of claim 1 wherein the upper portion has a handle means for inserting the device into the light path of the analytical instrument.

9. A method for retrofitting a flow cell optical analysis apparatus comprising a light source and a photo detector defining a first and a second end of an optical path, a vacuum source for drawing a liquid sample through a flow cell positioned in the optical path so that light from the light source passes through the sample, and means for analyzing data collected at the photo detector into a coagulation assay apparatus comprising the light source and the photo detector defining the ends of the optical path, a cuvette containing a liquid sample positioned in the optical path for passage of light from the light source through the liquid sample, a means for agitating the liquid sample and the means for analyzing data collected at the photo detector, the method for retrofitting comprising the steps of:

a) removing the flow cell from the apparatus;

b) replacing the flow cell with a cuvette holder comprising an upper portion having an opening for receiving and holding the cuvette; and a lower portion affixed to the upper portion and comprising a rotor housing and a rotor, the rotor having a permanent magnet mounted on a top surface thereof and a plurality of vanes, the rotor being rotatably mounted in the rotor housing; the rotor housing having a first bore in which the rotor is seated and second and third bores communicating the first bore with the exterior of the device, so that air flow may be induced from an external air pressure differential source across the first bore from the second bore to the third bore, the second and third bores being situated so as to direct the air flow at the plurality of vanes to cause rotation of the rotor within the first bore; wherein the rotation of the rotor in the rotor housing induces a magnetic field which causes co-rotation of the stirring bar.

\* \* \* \* \*